United States Patent [19]

Cantarero

[11] Patent Number: 5,294,767
[45] Date of Patent: Mar. 15, 1994

[54] DEVICE FOR DESTROYING HYPODERMIC NEEDLES

[75] Inventor: Antonio Cantarero, Incisa Valdarno, Italy

[73] Assignee: Libo-Medical S.r.l., Florence, Italy

[21] Appl. No.: 827,693

[22] Filed: Jan. 23, 1992

[30] Foreign Application Priority Data

Jan. 31, 1991 [IT] Italy ............... MI 91 A 000235

[51] Int. Cl.[5] ............................................. B23H 9/00
[52] U.S. Cl. ............................ 219/68; 75/10.65; 110/346
[58] Field of Search ............. 75/10.65; 110/346; 219/68; 128/419 R

[56] References Cited

U.S. PATENT DOCUMENTS 5,005,496  4/1991  Nagata ........................... 110/346
5,199,973  4/1993  Funk ............................... 75/580

Primary Examiner—Peter D. Rosenberg
Attorney, Agent, or Firm—Oliff & Berridge

[57] ABSTRACT

A portable device for the complete destruction of hypodermic needles includes a contact mechanism comprising two parts, a recess being formed in the two parts to receive an inserted needle. Behind the contact mechanism is a plate that contacts the inserted needle. A current source, such as a battery, is connected to the contact mechanism and to the plate so that a short circuit between the contact mechanism and the plate causes the inserted needle to melt.

19 Claims, 4 Drawing Sheets

DEVICE FOR DESTROYING HYPODERMIC NEEDLES

BACKGROUND OF THE INVENTION

The present invention relates to a device which completely destroys hypodermic needles by means of a short circuit which determines fusion of the metallic portion of the needle. Complete destruction is assured by a mechanical mechanism, the "lever-controlled mobile contact", which maintains a constant electrical contact and accompanies the movement of the needle until the latter is completely destroyed.

It is known how used hypodermic needles constitute a danger, since they can easily become vehicles for infection either through reuse of the needle itself or following involuntary puncture of the health worker charged with disposing of and destroying infected needles.

In order to obviate these difficulties, devices suitable for destroying the needles through use of a short cicuit which causes them to melt are used. In particular, the Patent Application no. GB-A-2211420 describes a device which uses a movable, V-shaped contact.

The devices currently in use present a number of disadvantages, due either to their large size, which makes portable use impossible (such use is particularly important in the case of needles to be destroyed in hospital wards or in out-of-doors sites in which infected needles are collected, after they have been left etc.); or, above all, to the fact that said devices do not totally destroy the needle but leave instead a residual part of the point which, however small, may nonetheless represent a danger to the user; or to the fact that said devices require that the user subject the needle to continuous, specific movements in order to maintain the contact which causes the short circuit and thus destruction of the needle.

SUMMARY OF THE INVENTION

The present invention makes it possible to overcome the disadvantages listed above and to completely destroy the needles, and consequently to make the syringe itself unserviceable, since the same will be irreparably deformed at the point of connection between the needle and the neck of the syringe.

These results are obtained thanks to a contact mechanism consisting of two parts, one of which may rotate with respect to the other.

BRIEF DESCRIPTION OF THE DRAWINGS

The characteristics and advantages of the invention are illustrated below with reference to FIGS. 1 through 5; the figures are illustrative but not limiting.

DETAILED DESCRIPTION OF THE PREFERRED EMBODIMENTS

Figure 1:
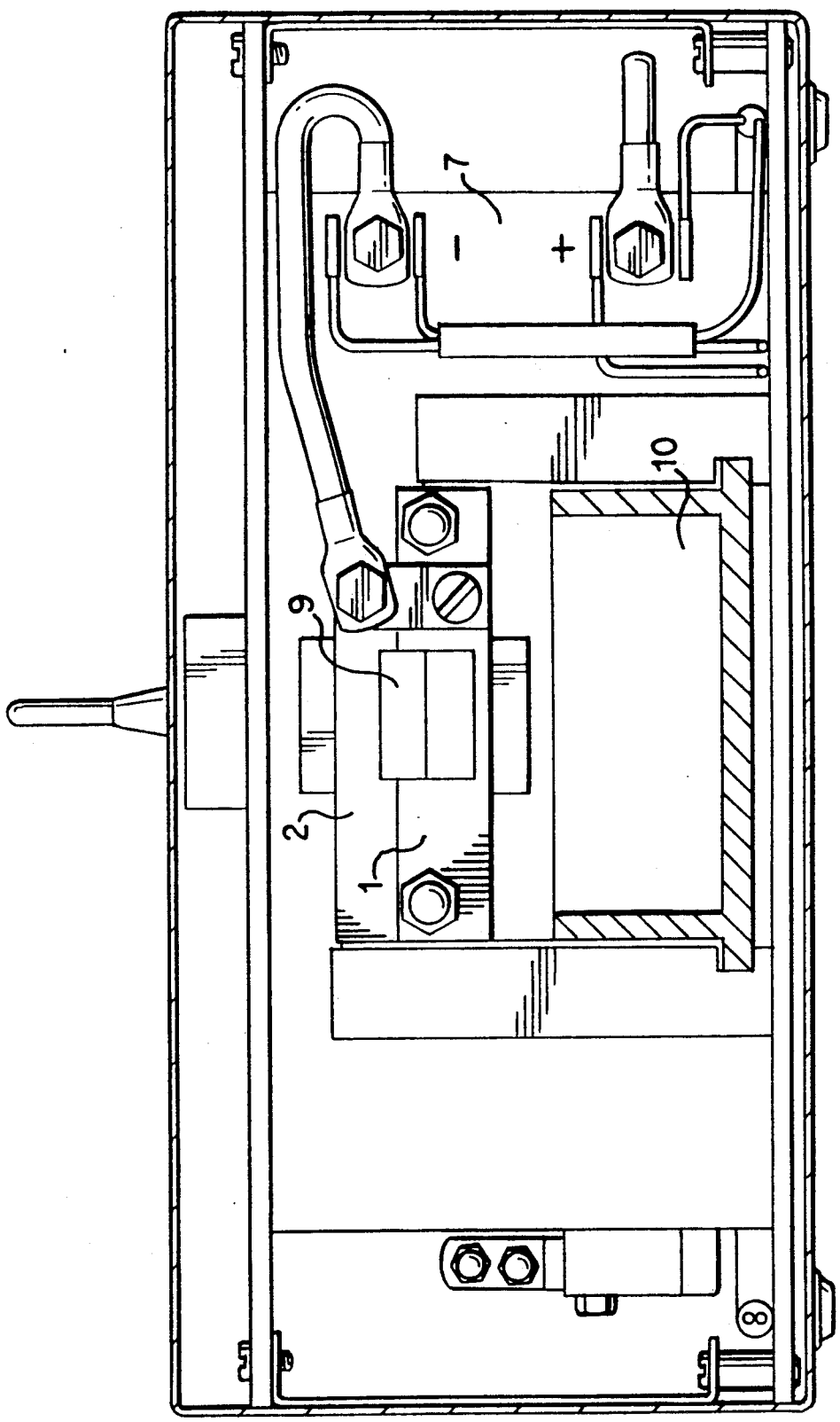
FIG. 1 shows a vertical section of the whole of the device according to the invention.
Figure 2B:
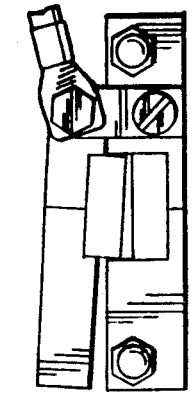
FIGS. 2(a)-2(b) show the contact mechanism in detail.
Figure 3B:
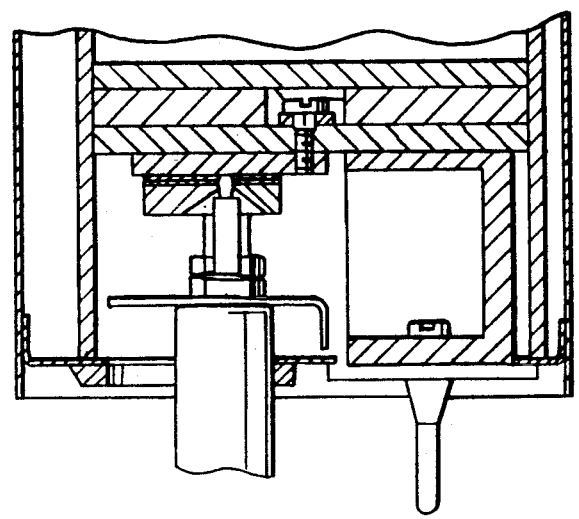
FIGS. 3(a)-3(b) show insertion and destruction of the needle.
Figure 2A:
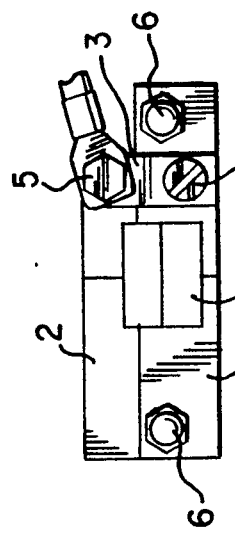
Figure 3A:
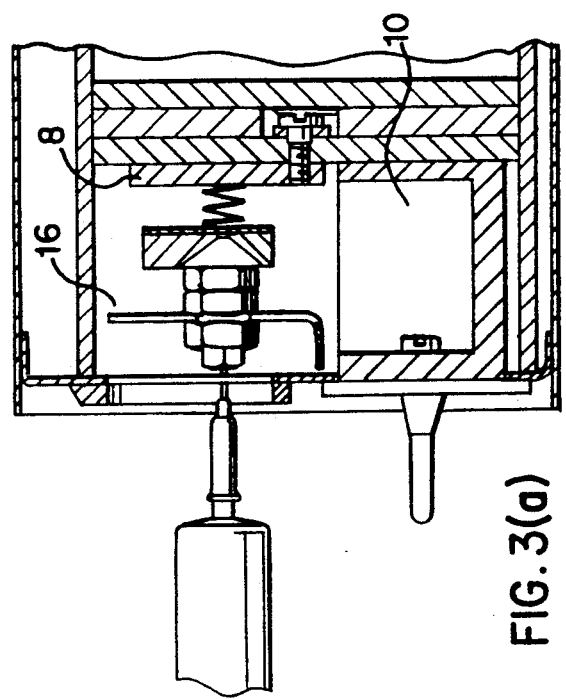
Figure 4:
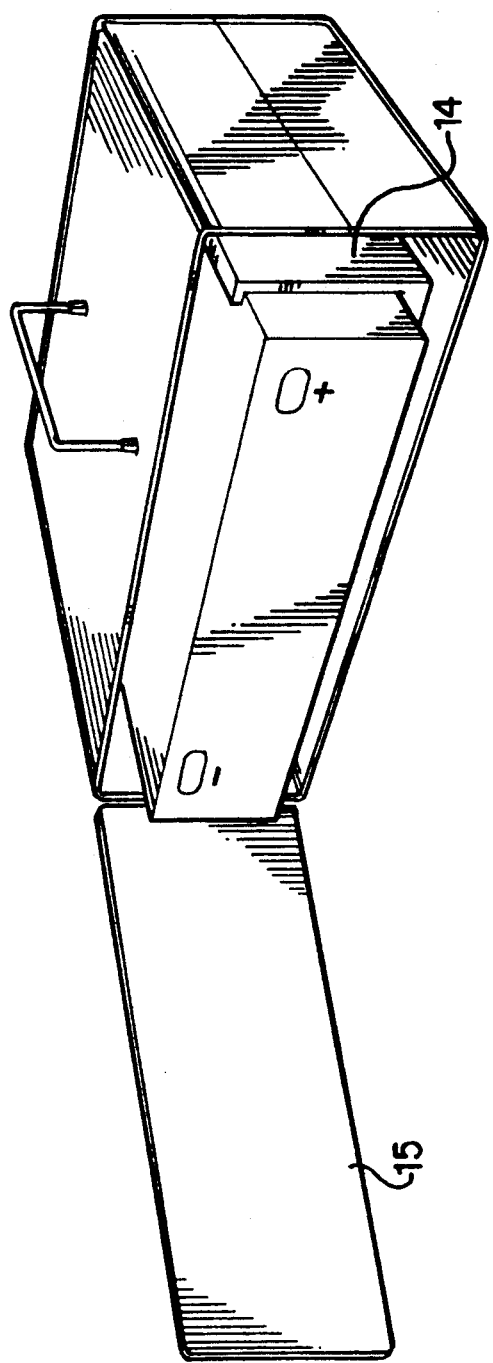
FIG. 4 shows a rear view of the device.

As can be seen in FIGS. 1 and 2(a), the contact mechanism consists of two metal parts 1 and 2 joined by a metal plate 3 which is connected to part 1 with a suitable fastening 4, for example a screw, and to part 2 with another fastening 5, for example a joint pin, such as to allow part 2 to rotate with respect to part 1.

The contact mechanism is connected to the frame of the device with suitable fastenings 6, for example joint pins, incorporating springs to allow movement of the contact mechanism along a longitudinal axis.

The fastening 5 is connected to one pole of battery 7, the second pole of which is connected to a ground plate 8.

Parts 1 and 2 of the contact mechanism each have, the one in correspondence to the other, a recess 9 shaped in the form of blades, with a maximum thickness at the cutting point of 0.5 mm. The cavity formed by profile 9 is protected by a metal plate 16, in order to protect against sparks caused by destruction of the needle and for obvious reasons of hygiene.

The metal parts of the contact mechanism may be made of any metal which is a good electrical conductor but preferable in nickel-plated copper, while the part of the contact which at the limit stop rests on the ground plate 8 is, obviously, coated with a non-conducting material.

Inserting the needle to be destroyed in the profiled part 9 and pushing until the ground plate 8 is touched establishes a short circuit and the needle begins to melt; continuing pushing causes the contact mechanism to slide on the spring joint pins 6 while the movable part 2 of the contact mechanism guarantees continuous contact with the needle, with no need for the user to "search for" the contact by continuously moving the needle, until the needle is completely destroyed.

According to one version of the invention, the movable part 2 of the contact mechanism may include, on the end opposite that which pivots, a second spring which, by exerting pressure in the direction of part 1, guarantees even better contact with the needle.

The fused metal parts are collected in the extractable container 10 for that purpose from which they may be easily disposed of. To remove the metal parts which may remain attached to plate 8 at the end of the operation, a blade 11 sliding through an opening 12 in the upper part of the device in correspondence to the surface of the ground block 8 and scrape any residues off said surface. Opening 12 is closed by a spring shoe 13. On the wall of the device, in correspondence to the blade profile 9, there is a circular hole for inserting the syringe. In a preferred embodiment, said hole is eccentric so as to permit insertion of syringes on which the needle is in a position which is not coaxial with respect to the body of the syringe, as is the case with syringes used for taking blood samples.

Figure 5B:
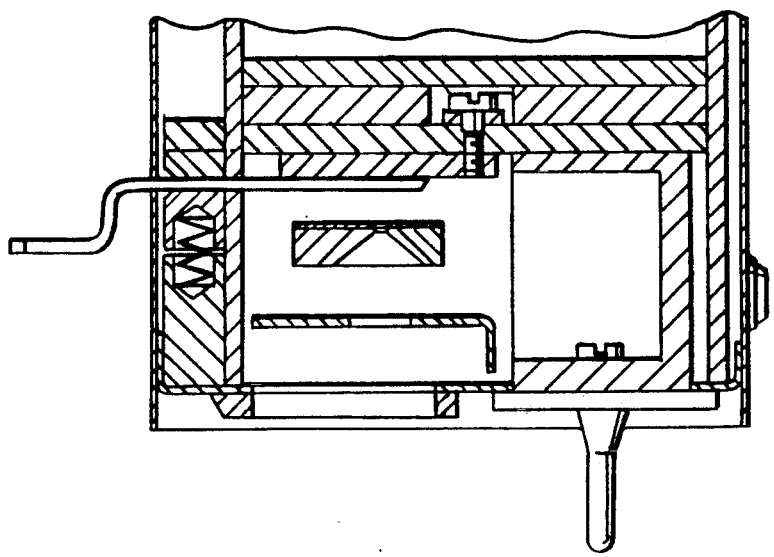
FIGS. 5(a)-5(b) show the system for cleaning the electrical contacts, in detail.
Figure 5A:
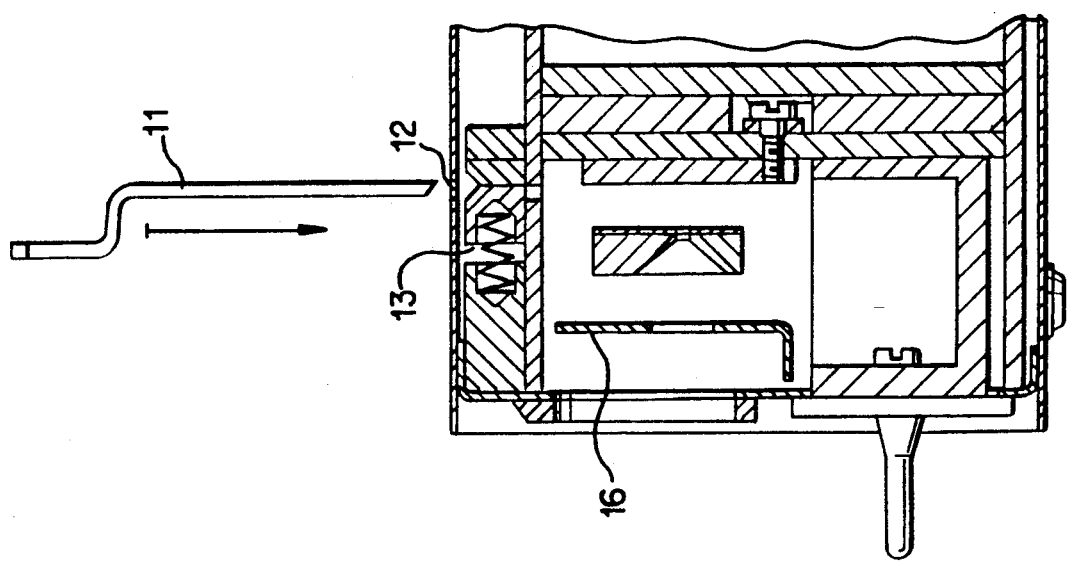

The battery 7, normally 6 V, may be installed on special guides 14 so as to make it easier to replace through access door 15 which closes the rear of the device as shown in FIG. 5.

While this invention has been described in conjunction with a specific embodiment thereof, it is evident that many alternatives, modifications and variations will be apparent to those skilled in the art. Accordingly, the preferred embodiment of the invention as set forth herein is intended to be illustrative, not limiting. Various changes may be made without departing from the spirit and scope of the invention as defined in the following claims.

I claim:

1. A portable device for the complete destruction of hypodermic needles between two contacts through an electrical short-circuit, comprising:

a first contact wherein said first contact is connected to a battery supplying current, is attached to a frame of the device with two fastenings incorporating springs which allow movement along a longitudinal axis, and comprises two metal parts which present, one in correspondence with the other, a recess, said parts being connected by a metal plate attached to the parts by fastenings and connected to one of the parts by one of the fastenings which allows said one of the parts to rotate with respect to the other of the parts, and;

a second contact, the second contact comprising a ground plate located behind the recess.

2. The device according to claim 1 in which blades bordering the recess have a maximum thickness of 0.5 mm at a cutting point.

3. The device according to claim 1 in which the fastenings are joint pins.

4. The device according to claim 1 in which the metal parts and the metal plate are formed of nickel-plated copper.

5. The device according to claim 1 in which the rotatable part has, at an end opposite an end that has a pivot about which the rotatable part rotates, a spring which exerts pressure in the direction of the rotatable part.

6. The device according to claim 1 further comprising a container for collection of melting residues.

7. The device according to claim 1, further comprising a system for cleaning the contacts, comprising a blade capable of sliding in an opening 1) cut in an upper part of the device in correspondence with a surface of the ground plate and 2) closed by a spring shoe.

8. The device according to claim 1 in which the battery is installed on guides and may be extracted through a rear access door.

9. The device according to claim 1 in which the battery is a 6 Volt lead battery.

10. A needle disposal device, comprising:

a contact mechanism comprising at least two relatively movable parts;

a recess, formed in the at least two parts, that receives an inserted needle;

a plate, located behind the recess, that contacts the inserted needle; and a current source connected to the contact mechanism and the plate, wherein current flowing between the contact mechanism and the plate through the inserted needle causes the inserted needle to melt.

11. The needle disposal device of claim 10, wherein the plate is a ground plate, the at least two parts are fastened to a connecting plate by at least one fastening, and at least one of the two parts pivots on the connecting plate to allow the inserted needle to contact the ground plate.

12. The needle disposal device of claim 10, wherein the contact mechanism is movable in a direction of needle insertion.

13. The needle disposal device of claim 12, wherein the contact mechanism is connected to a frame of the device by at least one fastening comprising a spring that is biased in a direction parallel to the direction of needle insertion.

14. The needle disposal device of claim 10, wherein the recess is bordered by blade-like portions of the at least two parts, the blade-like portions each having an edge which contacts the inserted needle at a cutting point and which has a maximum thickness of 0.5 mm at the cutting point.

15. The needle disposal device of claim 10, further comprising a plate cleaning device comprising a blade that cleans debris from the plate.

16. The needle disposal device of claim 15, wherein the blade slides in an opening in a frame of the device.

17. A needle disposal device, comprising:

a contact mechanism that reciprocates in a direction substantially parallel to a direction in which a needle is inserted into the device;

a surface, located behind the contact mechanism, that contacts the inserted needle; and a current source connected to the contacting mechanism and the surface, wherein current flowing between the contact mechanism and the surface through an inserted needle causes the inserted needle to melt.

18. The needle disposal device of claim 17, wherein the contact mechanism comprises at least two relatively movable parts, further wherein a recess that receives the inserted needle is formed in the at least two parts.

19. The needle disposal device of claim 18, wherein the surface is the surface of a ground plate, the at least two parts are fastened to a connecting plate, and at least one of the two parts pivots on the connecting plate to allow the inserted needle to contact the surface of the ground plate.

* * * * *